United States Patent [19]

Weber

[11] Patent Number: 5,286,255
[45] Date of Patent: Feb. 15, 1994

[54] SURGICAL FORCEPS

[75] Inventor: Robert M. Weber, Diamond Bar, Calif.

[73] Assignee: Linvatec Corporation, Largo, Fla.

[21] Appl. No.: 737,338

[22] Filed: Jul. 29, 1991

[51] Int. Cl.$^5$ .................... A61B 17/28; A61B 17/32
[52] U.S. Cl. .................... 604/22; 606/170; 606/205; 606/208; 128/752
[58] Field of Search .............. 606/205, 2067, 207, 606/208, 170, 167; 128/751, 752; 604/22

[56] References Cited

U.S. PATENT DOCUMENTS

| 385,076 | 6/1888 | Stohlmann | 606/208 X |
|---|---|---|---|
| 2,568,234 | 9/1951 | Haufrect | 606/174 |
| 4,522,206 | 6/1985 | Whipple et al. | |
| 4,662,371 | 5/1987 | Whipple et al. | |
| 4,944,093 | 7/1990 | Falk | 606/174 |
| 4,986,825 | 1/1991 | Bays et al. | |
| 5,009,661 | 4/1991 | Michelson | 606/170 |

FOREIGN PATENT DOCUMENTS

| 0119405 | 9/1984 | European Pat. Off. |
| 0316816 | 5/1989 | European Pat. Off. |
| 8518482 | 10/1985 | Fed. Rep. of Germany |
| 3601166 | 7/1987 | Fed. Rep. of Germany |
| 8704161 | 10/1987 | Fed. Rep. of Germany |

Primary Examiner—Michael H. Thaler

[57] ABSTRACT

A surgical forceps particularly useful in least invasive surgery includes an elongate probe formed of an outer tubular member and an inner member movable in the outer probe member, stationary and movable jaws coupled with the distal ends, respectively, of the outer and inner probe members, and a handle squeezable to move the movable jaw relative to the stationary jaw to rearwardly or forwardly cut tissue or grasp tissue. A force diverting mechanism is responsive to the force applied to the handle exceeding a predetermined force to provide the surgeon with an indication of the excessive force and protects the jaw components at the distal end of the surgical forceps. A suction passage is formed in the forceps for aspirating cut tissue and assisting the positioning of tissue between the jaws, and suction can be produced continuously or controlled via the handle. The handle includes locking and latching mechanisms to hold the jaws in a closed position.

13 Claims, 2 Drawing Sheets

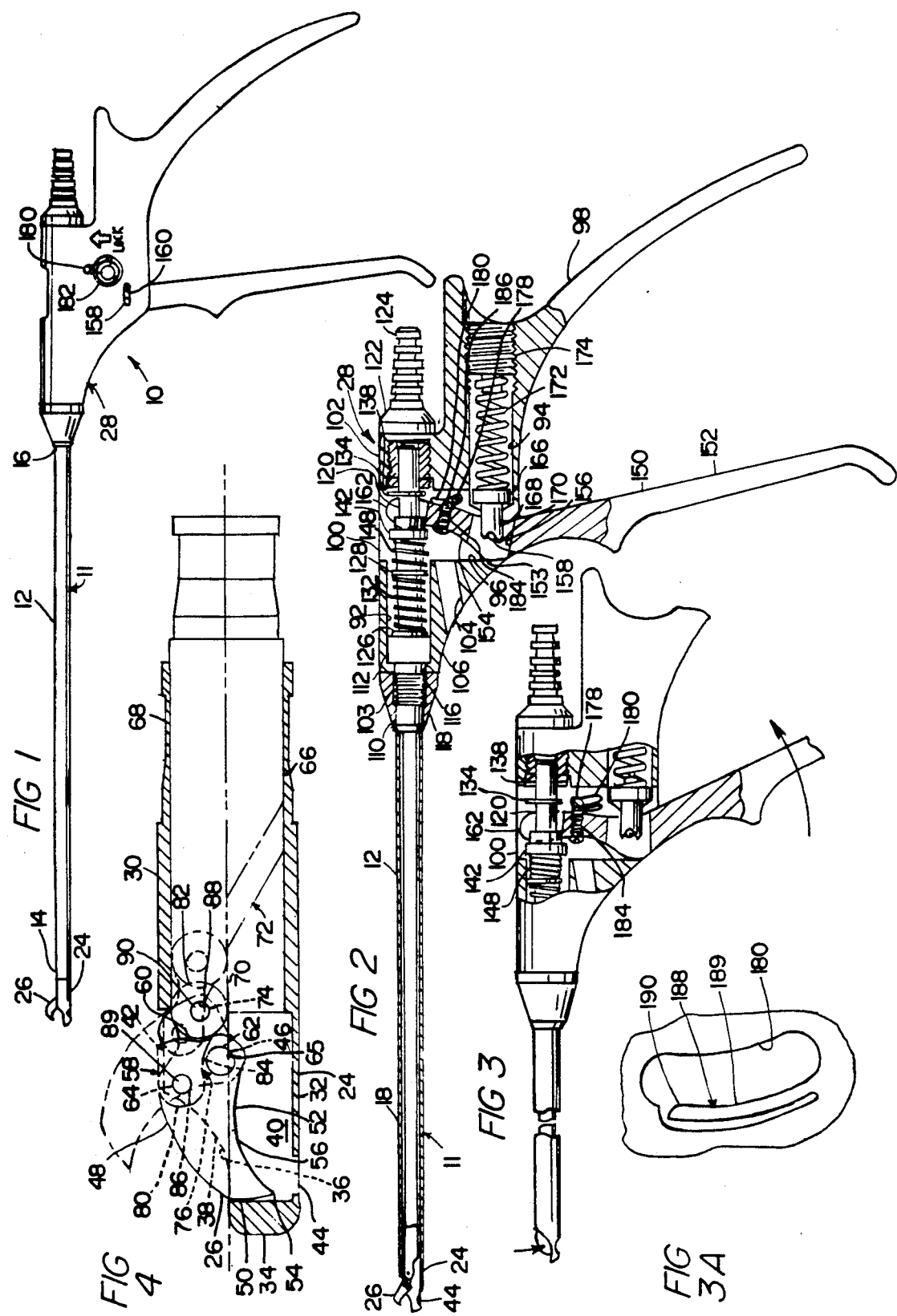

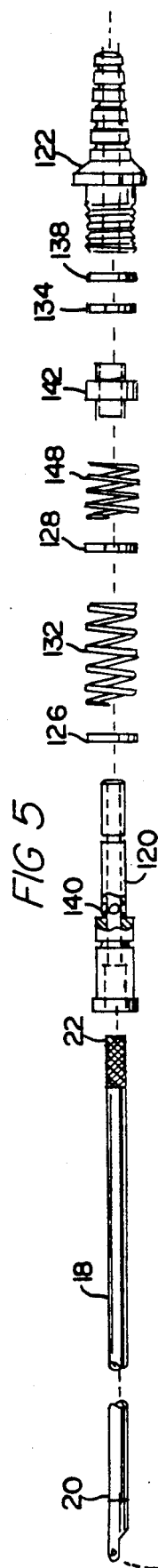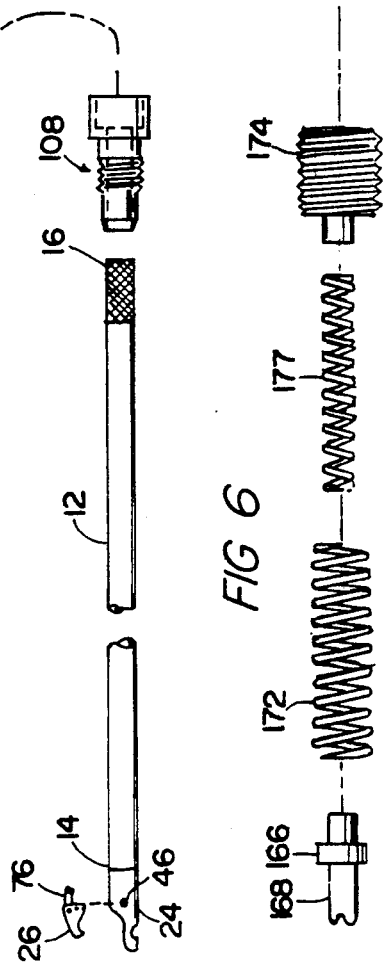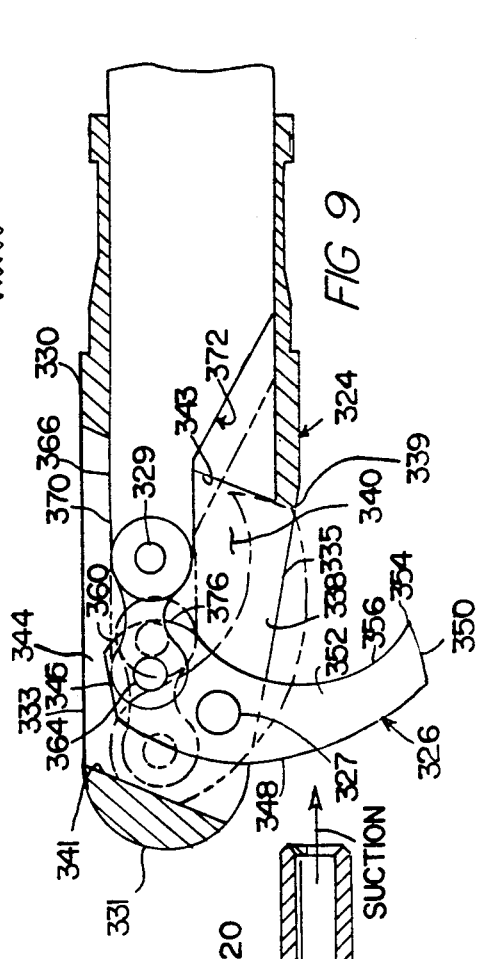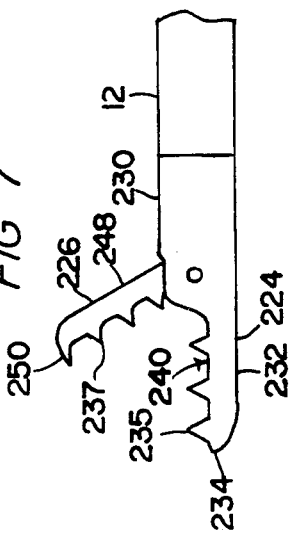

SURGICAL FORCEPS

BACKGROUND OF THE INVENTION

1. Field of the Invention

The present invention pertains to intra-articular devices and, more specifically, to surgical suction forceps for cutting or grasping tissue and applying suction.

2. Description of the Prior Art

Intra-articular surgical devices for cutting and aspirating tissue from the body are well known, as exemplified by the C-Cutter of the IntraArc Arthroscopy Blade System of Concept and as further exemplified by U.S. Pat. No. 4,986,825 to Bays et al and U.S. Pat. Nos. 4,662,371 and 4,522,206 to Whipple et al. Such surgical devices or instruments typically include a movable jaw and a stationary jaw mounted, respectively, on distal ends of relatively movable inner and outer tubular members to permit the jaws to engage tissue when the movable jaw is moved relative to the stationary jaw in response to movement of the inner tubular member produced by a drive at the proximal end of the instrument. With the inner and outer tubular members having an elongate configuration, surgical cutting and grasping instruments characterized by cooperating, closable jaws have particular utility in closed, or least invasive, surgical procedures, including arthroscopy, by allowing the jaws to be positioned to engage tissue at a surgical site via insertion through a small portal with minimal trauma. Such instruments are referred to herein as suction forceps. The jaws of such suction forceps can be driven either manually, as exemplified by the Whipple et al patents and by the various Shutt forceps of Concept, or with a power drive as exemplified by the Concept IntraArc Arthroscopy Power System and C-Cutter and the Bays et al patent, the drive serving to move the inner elongate member relative to the outer elongate member to, in turn, open and close the jaws.

Some of the disadvantages of prior art suction forceps are that, when the jaws are operated or driven manually by a pivotal handle, components at the distal end can be broken if excessive force is applied to the handle creating the opportunity for severed parts to be introduced at the surgical site, and that the movable jaw is unable to scoop up and cut tissue in a rearwardly directed cutting action and is generally incapable of readily cutting tissue positioned so as to require a "backbiting" cutting action. Additionally, the movable jaws in manually operable suction forceps frequently cannot be effectively locked in a "closed" position for safety in handling the instruments and for enhanced manipulation in closely confined surgical sites. Locks proposed in the past for securing manually movable operating handles in a position corresponding to a closed position for the movable jaws are structurally and functionally complicated and are incompatible for use under the time constraints of surgery. Moreover, the locks frequently are accidentally defeated during normal handling of the surgical instruments and, therefore, are unreliable. When cooperating, closable jaws are used to grasp tissue, the grasping jaws must be securely closed around the tissue to obtain a firm holding grip thereon. In many cases, it is difficult to reach tissue with the grasping jaws o to initially draw tissue between the jaws when the jaws are positioned proximate, but in less than direct engagement with, tissue.

SUMMARY OF THE INVENTION

Accordingly, it is a primary object of the present invention to overcome the above mentioned disadvantages of prior art suction forceps for cutting and/or grasping tissue.

Another object of the present invention is to divert force applied to a handle of a surgical forceps when the applied force exceeds a predetermined force to provide a tactile indication of excess force via the handle and to prevent damage to and breakage of components at the distal end of the forceps.

The present invention has another object in the control of suction through a suction forceps by manipulation of handle grip members.

It is also an object of the present invention to provide a suction forceps having cooperating, closable cutting jaws for cutting tissue at a surgical site while suction is provided at the surgical site continuously with suction produced at the jaws via a suction passage in the suction forceps.

A further object of the present invention is to provide a suction forceps having cooperating, closable grasping jaws for grasping tissue while suction is produced at the grasping jaws via a suction passage in the suction forceps to initially draw tissue between the grasping jaws when the grasping jaws are in an open position.

Additionally, it is an object of the present invention to tactilely indicate when a force applied to hand grip members exceeds a predetermined force to prevent damage and/or breakage of components at the distal end of a surgical forceps.

It is also an object of the present invention to lock cooperating, closable jaws of a surgical forceps in a closed position while preventing locking when the jaws are not in the closed position and preventing accidental release from the locked position.

Furthermore, it is an object of the present invention to provide a suction forceps having a movable cutting jaw mounted on a distal end thereof for movement through an opening in a stationary cutting jaw to position a distal end of the movable cutting jaw adjacent a proximal end of the opening to cut tissue through the opening in a rearward cutting action.

Some of the advantages of the present invention over the prior art are that the surgical forceps is suitable for use with diverse cutting jaws as well as grasping jaws, is manually operable in a manner familiar to surgeons and produces a fast and efficient cutting action with unconstricted aspiration of cut tissue while damage to components during use is minimized.

The surgical forceps of the present invention is generally characterized by an outer elongate tubular member having a distal end and a proximal end and an inner elongate tubular member slidably disposed in the outer tubular member and having a distal end and a proximal end. A stationary jaw is disposed at the distal end of the outer member, and a movable jaw is pivotally mounted on the stationary jaw. A cam mechanism translates sliding movement of the inner member relative to the outer member into pivotal movement of the movable jaw relative to the stationary jaw between an open position and a closed position to engage tissue between the jaws. The proximal ends of the inner and outer members are disposed in a handle body containing an actuating mechanism for sliding the inner member within the outer member in response to pivotal movement of a hand grip member. The actuating mechanism includes a tubular shaft having a first end receiving the proximal end of the inner member and a second end slidably disposed in a suction fitting in the handle body for producing suction through the shaft and the inner member when the suction fitting is connected to a vacuum source, the tubular shaft being biased to maintain the jaws in the open position. A push ring is slidably disposed on the tubular shaft in engagement with the movable grip member and is biased to uncover holes in the tubular shaft in alignment with a window in the handle body to divert suction from the jaws. Pivotal movement of the grip member causes the push ring to slide relative to the tubular shaft to cover the holes and establish suction at the jaws. Suction is distributed around the jaws to initially draw tissue therebetween, and further movement of the grip member causes the tubular shaft and, therefore, the inner member, to slide relative to the outer member to pivot the movable jaw to the closed position. When the jaws are grasping jaws, suction at the jaws supplements the holding force of the jaws; and, when the jaws are cutting jaws, cut tissue is aspirated through an unconstricted suction passage. When cutting jaws are utilized, an aperture is provided in the stationary jaw in communication with the suction passage and the surgical site to produce suction at the surgical site continuously through the jaws. When a force exceeding a predetermined force is applied to the handle, the surgeon is tactilely and visually alerted to the application of potentially damaging operating forces. A lock is movably mounted in the handle body for selective movement to a locked position when the handle is in a position corresponding to the closed position for the jaws, and the lock is prevented from being moved to the locked position when the jaws are not in the closed position. A latch integral with the handle body is biased to secure the lock in the locked position. The jaws can be used for cutting tissue in a forwardly directed cutting action or in a rearwardly directed, or "backbiting", cutting action or for grasping tissue.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a side view of a suction cutting forceps according to the present invention.

FIG. 2 is a partial longitudinal sectional view of the suction forceps of FIG. 1.

FIG. 3 is a broken, partial longitudinal sectional view of the suction forceps of FIG. 1 showing cutting jaws locked in a closed position.

FIG. 3A is a broken side view of a side wall of a handle body of the suction forceps of FIG. 1.

FIG. 4 is a side view, partly in section, of a distal end of the suction forceps of FIG. 1.

FIG. 5 is an exploded view of inner and outer tubular members and the actuating mechanism of the suction forceps of FIG. 1.

FIG. 6 is an exploded view of an overload force indicator of the suction forceps of FIG. 1.

FIG. 7 is a broken side view of a distal end of a suction grasping forceps according to the present invention.

FIG. 8 is a partial longitudinal sectional view of the actuating mechanism of the suction forceps of FIG. 1.

FIG. 9 is a side view, partly in section, of a distal end of a modification of the suction cutting forceps according to the present invention.

DESCRIPTION OF THE PREFERRED EMBODIMENTS

A surgical suction cutting forceps 10 according to the present invention is shown in FIGS. 1-6 and includes an elongate probe 11 formed of outer elongate tubular member 12 having a distal end 14 and a proximal end 16 and an inner elongate tubular member 18 slidably disposed within the outer tubular member 12 and having a distal end 20 and a proximal end 22. A stationary cutting jaw 24 and a movable cutting jaw 26 are disposed, respectively, at the distal ends 14 and 20, and the proximal ends 16 and 22 are received in a handle body 28. As shown in FIG. 4, the stationary cutting jaw 24 includes a tubular end 30 joined to the distal end 14 of the outer member 12, such as by brazing or the like, a semi-cylindrical wall 32 joined to the lower part of the tubular end 30 and an end wall 34, arcuate in configuration when viewed from above, joined to the semi-cylindrical wall 32. A surface 36 on the end wall 34 and the semi-cylindrical wall 32 curves upwardly in the proximal direction from the end wall 34 to an upper part of the tubular end 30 to define a peripheral cutting edge on the inner surface of the stationary cutting jaw 24 circumscribing an opening 38 on the upper side of the semi-cylindrical wall leading into a chamber 40. A rectangular slot 42 intersecting the opening 38 is formed in the upper part of the tubular end 30 to extend lengthwise from the opening 38 in the proximal direction. An aperture or opening 44 is formed in the lower side of the semi-cylindrical wall 32 adjacent an inner surface of the end wall 34 in fluid communication with the chamber 40, the aperture 44 having a distal edge aligned with a distal portion of the cutting edge formed by opening 38. A bore 46 is formed through the tubular end 30 transverse to the longitudinal axis of the outer member 12 and in alignment with the slot 42, and the longitudinal axis of the bore 46 is positioned between the longitudinal axis of the outer member 12 and the slot 42.

The movable cutting jaw 26 includes a curved top wall 48 joined to a distal end wall 50 that is arcuate in configuration when viewed from below and side walls 52 joined to end wall 50 and top wall 48. An arcuate cutting edge 54 is formed on the end wall 50 of a cutting portion of the movable jaw, and inwardly curving side cutting edges 56 are formed on the side walls 52 for movement past the cutting edge on the inner surface of the stationary cutting jaw 24. An opening 58 is formed in the top wall 48 communicating with a recess extending laterally between the side walls 52 such that the side walls 52 define spaced, parallel ears 60 on an actuating portion of the movable jaw. Bores 62 and 64 are formed transversely through the ears 60 in spaced parallel relation. The bore 62 is aligned with the bore 46 in the stationary cutting jaw 24, and a pivot pin 65 is inserted through the aligned bores 62 and 46 to pivotally mount the movable cutting jaw 26 on the stationary cutting jaw 24 at a pivot point disposed proximally of aperture 44.

A cam 66 is disposed at the open distal end 20 of the inner member 18 and includes a cylindrical body 68 joined coaxially to the distal end 20, such as by brazing and the like, and a pair of spaced, parallel prongs 70 projecting longitudinally in a distal direction from an upper part of the cylindrical body 68. The end of the cylindrical body 68 is open and angularly disposed with the longitudinal axis of the inner member 18, and the open end 72 communicates with the chamber 40 and the lumen of the inner member 18. A bore 74 is formed transversely through the prongs 70, and the longitudinal axis of the bore 74 is disposed laterally above, of the longitudinal axis of the inner member 18. An actuator or cam follower 76 for translating sliding movement of the inner member 18 into pivotal movement of the movable cutting jaw 26 includes a rigid plate of substantially constant thickness having a circular jaw end 80 and a circular cam end 82 joined to the jaw end 80 by a central neck 84. A bore 86 is formed centrally in the jaw end 80, and a bore 88 is formed centrally in the cam end 82. The jaw end 80 is positioned between the ears 60 on the movable cutting jaw 26 to align the bore 86 with the bore 64, and a pivot pin 89 is inserted through the aligned bores 86 and 64 to pivotally connect the actuator 76 with the actuating portion of the movable cutting jaw 26. The cam end 82 is positioned between the prongs 70 on the cam 66 to align the bore 88 with the bore 74, and a pivot pin 90 is inserted through the aligned bores 88 and 74 to pivotally connect the actuator 76 with the cam 66, the aperture 72 in the cam 66 being proximally spaced from proximal ends of the stationary and movable jaws 24 and 26.

As shown in FIGS. 2 and 3, the handle body 28 has an upper interior through passage 92 receiving the proximal ends 16 and 22, respectively, of the outer and inner members 12 and 18, a lower interior passage 94 disposed parallel to the upper passage 92 and an intermediate interior passage 96 perpendicularly joining the upper and lower passages 92 and 94. A fixed hand grip member or handle 98 is integrally joined to the handle body 28 adjacent a rearward end of the passage 94 and depends rearwardly from the handle body 28. A window 100 is formed in a top wall 102 of the handle body 28 in alignment with the intermediate passage 96 and opening into the upper passage 92. A port 104 angularly disposed with the intermediate passage 96 extends through a front wall 106 of the handle body 28 in communication with the intermediate passage 96. A cylindrical nose plug 108 is disposed at a forward end of the upper passage 92 and includes a first bore section 110 securely receiving the proximal end 16 of the outer member 12 and a second bore section 112 having an enlarged annular rim extending from a rearward side of an interior radial shoulder 116 at the forward end of the upper passage 92. The first bore section 110 is externally threaded along part of the longitudinal length thereof for receiving an internally threaded nose cap 118 positioned in engagement with a forward side of the shoulder 116. A tubular shaft 120 is slidably disposed in the upper passage 92 and includes a forward end slidably disposed in the second bore section 112 of the nose plug 108 and securely receiving the proximal end 22 of the inner member 18. A rearward end of the cylindrical shaft 120 is slidably received in a hollow suction fitting 122 threadedly secured in a rearward end of the upper passage 92. A tubular extension 124 on the suction fitting 122 allows the suction fitting to be connected to a vacuum source to produce suction through the tubular shaft 120, the inner member 18 and the cam 66, which define a continuous suction passage having no constrictions therein. The tubular shaft 120 extends through an annular retaining washer 126 positioned in abutment with the annular rim of the second bore section 112 of the nose plug 108, and a generally C-shaped clip 128 is secured on the tubular shaft 120 in a recess spaced rearwardly from the retaining washer 126. A coiled actuating spring 132 is disposed around the tubular shaft 120 between the retaining washer 126 and the clip 128 and is mounted in compression to urge the tubular shaft 120 and, therefore, the inner member 18, in a rearward direction. A generally C-shaped stop member 134 is secured on the tubular shaft 120 in a recess rearwardly spaced from the clip 128 such that the stop 134 abuts an annular washer 138 positioned adjacent the suction fitting 122 to limit rearward movement of the tubular shaft 120 under the biasing force of the actuating spring 132. As shown in FIG. 8, suction diverting holes 140 are formed in the tubular shaft 120 at 90° spaced locations rearwardly spaced from the clip 128 to be disposed in the intermediate passage 96 in the handle body 28 in alignment with the window 100. A cylindrical push ring 142 is slidably carried on the tubular shaft 120 for movement between the clip 128 and the stop 134 and includes an enlarged flange defining a forward shoulder 144 and a rearward shoulder 146. A coiled suction spring 148 is disposed around the tubular shaft 120 and mounted in compression between the clip 128 and the forward shoulder 144 to bias the push ring 142 in the rearward direction and expose the holes 140 as shown in FIG. 8.

A movable hand grip member or handle 150 is pivotally mounted on the handle body 28 and includes a hand grip 152 depending angularly from an elbow or mounting section 153 and an actuating arm 154 angularly joined to the elbow 153 to extend upwardly therefrom. The actuating arm 154 is positioned in the intermediate passage 96 of the handle body 28, and a recess 156 in the elbow 153 is longitudinally aligned with the lower passage 94. A bore is formed through the elbow 153 transverse to and longitudinally aligned with the longitudinal axis of the lower passage 94. As shown in FIG. 1, tracks or slots 160 are formed in opposing side walls of the handle body 28 in lateral alignment with the bore in the elbow 153. A pivot pin 158 is disposed in the bore in the elbow 153, and opposing ends of the pivot pin 158 are slidably disposed in the tracks 160 to be visible along the side walls of the handle body 28. A pair of spaced, parallel fingers 162 are defined on the actuating arm 154, and the tubular shaft 120 is longitudinally disposed between the fingers 162 such that the rearward shoulder 146 of the push ring 142 is biased by the suction spring 148 into engagement with the fingers 162 and urges the fingers 162 rearwardly against the stop 134 as shown in FIG. 2.

As shown in FIGS. 2 and 6, an overload force diverter and indicator mechanism includes a circular disk 166 slidably disposed in the lower passage 94 and an elongated cylindrical holder 168 projecting forwardly from the center of the disk 166 into the recess 156 in the elbow 153. A notch 170 is formed in a forward end of the holder 168, and the pivot pin 158 is held within the notch 170. A force overload coiled spring 172 is mounted in compression in the lower passage 94 between the disk 166 and a cylindrical compressor 174 threadedly received in the lower passage 94. The compressor 174 selectively maintains the overload spring 172 in compression such that the overload spring 172 biases the disk 166 against a tapered forward end of the lower passage 94 to permit the holder 168 to position the ends of the pivot pin 158 at forwardmost ends of the tracks 160 and the elbow 153 against a forward wall of the intermediate passage 96. For additional strength, a second overload spring 177, as illustrated in FIG. 6, can be disposed within the spring 172 to engage the disk 166 and the compressor, respectively. The biasing force of the overload spring against the disk 166 and, therefore, the pivot pin 158, is controlled by adjusting the compressor 174 to maintain the pivot shaft 158 at the forwardmost ends of the tracks 160 and the elbow 153 against the forward wall of the intermediate passage 96 When applied force to the grip members is less than a predetermined force.

As shown in FIGS. 1, 2 and 3, a locking pin 178 is disposed transversely in the intermediate passage 96, and opposing ends of the locking pin 178 project laterally from the side walls of the handle body 28. A curved slot 180 is formed in each of the side walls of the handle body 28 to slidably receive the opposing ends of the locking pin 178, and end caps 182 are provided on the opposing ends of the locking pin 178 exteriorly of the side walls to permit the end caps 182 to be manually grasped for moving the locking pin 178 within the intermediate passage 96 as guided by the slots 180. A plunger 184 is mounted in a hole in the actuating arm 154 of the movable handle 150 medially between the elbow 153 and the fingers 162. The plunger 184 includes a tip 186 positioned in the path of movement for the locking pin 178 and blocking movement of the locking pin 178 when the locking pin 178 is disposed at the lowermost ends of the slots 180 and the movable handle 150 is biased against the stop 134 as shown in FIG. 2. As shown in FIG. 3, the plunger 184 moves with the movable handle 150 when the movable handle 150 is rotated or pivoted about pivot pin 158 to position the tip 186 beyond the path of movement for the locking pin 178 and permit the locking pin 178 to be moved from the lowermost to the uppermost ends of the slots 180. As shown in FIG. 3A, curved spring latches 188 are integrally formed in the side walls of the handle body 28 along forward edges of the slots 180 and are biased into the slots 180. The spring latches 188 include curved spring arms 189 biased toward rearward edges of the slots 180 and rounded beads 190 at upper ends of the spring arms 189 for engaging and securing the locking pin 178 in a locked position at the uppermost ends of the slots 180. The biasing force of the spring arms 189 can be overcome by manually moving the locking pin 178 from the uppermost to the lowermost ends of the slots 180.

A modification of the suction forceps according to the present invention for use in grasping, rather than cutting, tissue is accomplished by substituting grasping jaws for the cutting jaws 24 and 26 at the distal end of probe 11 as illustrated in FIG. 7. The grasping jaws include a stationary grasping jaw 224 mounted on the distal end 14 of the outer probe member 12 and a movable grasping jaw 226 mounted relative to the stationary grasping jaw 224 in the manner previously described in connection with the cutting jaws 24 and 26. The stationary grasping jaw 224 has a tubular end 230 joined to distal end 14 of the outer member 12, a semi-cylindrical wall 232 joined to a lower part of the tubular end 230 and an end wall 234 that is arcuate in configuration when viewed from above joined to the semi-cylindrical wall 232. A plurality of triangular shaped grasping teeth 235 are disposed in longitudinal alignment on opposing lateral sides of the semi-cylindrical wall 232, and a chamber 240 is defined in the stationary grasping jaw 224 between the lateral sides of the semi-cylindrical wall 232. The movable grasping jaw 226 includes a semi-cylindrical top wall 248 joined to an end wall 250 that is arcuate in configuration when viewed from below and a plurality of triangular shaped grasping teeth 237 disposed in longitudinal alignment on opposing lateral sides of the semi-cylindrical wall 248 for cooperative interengagement with the grasping teeth 235 to grasp tissue when the movable grasping jaw 226 is pivoted relative to the stationary grasping jaw 224 by the actuator 76 and the cam 66 translating sliding movement of the inner member 18 into pivotal movement of the movable grasping jaw 226.

A modification of the suction cutting forceps according to the present invention for backbiting or rearwardly directed cutting is illustrated in FIG. 9 and includes a stationary cutting jaw 324 and a movable cutting jaw 326 disposed on the distal end of probe 11 in place of jaws 24 and 26. The stationary cutting jaw 324 has a tubular end 330 joined to the open distal end of the outer probe member, a rounded forward nose 331 joined tangentially to an upper part of the tubular end 330 by a semi-cylindrical upper wall 333 and angularly to a lower part of the tubular end 330 by a semi-cylindrical lower wall 335. An opening 338 is formed in the bottom of the lower wall 335 to define a cutting edge on the inner surface thereof including a proximal portion 339, and the opening 338 leads into a chamber 340 in the stationary cutting jaw 324 communicating with the aperture 372 in the cam 366 mounted on the open distal end of the inner probe member and having a distal wall 341 and a proximal wall 343. An aperture 344 is formed through a top of the upper wall 333 in communication with the chamber 340 and angularly offset from the opening 338. The movable cutting jaw 326 includes a curved top wall 348 joined to a end wall 350 that is arcuate in configuration and side walls 352 joined to the end wall 350 and the top wall 348. A pivot pin 327 extends through the stationary jaw 324 and the side walls 352 of the movable jaw transverse to the longitudinal axis of the inner member 18 to pivotally mount the movable jaw 326 on the stationary jaw 324 at a pivot point disposed distally of the proximal cutting edge portion 339 of opening 38. An arcuate cutting edge 354 is formed on the end wall 350, and inwardly curving side cutting edges 356 are formed on the side walls 352 for movement past the cutting edge on the inner surface of the stationary cutting jaw 324. A recess is formed in the proximal end of the movable jaw 326 and extends laterally between the side walls 352 such that the side walls 352 define spaced, parallel ears 360. The end of the actuator is positioned between the ears 360 to align the bore in the end with a bore extending transversely through the ears 360, and a pivot pin 364 is inserted through the aligned bores to pivotally connect the actuator with the movable cutting jaw 326 while a pivot pin 329 pivotally mounts the cam end of the actuator between the ears of the cam 366. Flats 345 are formed on the prongs 360 along a proximal end wall of the movable jaw 326.

In operation, the probe 11 having jaws appropriate for the procedure to be performed, for example cutting jaws 24 and 26, is introduced at a surgical site, such as through a small portal in endoscopic surgery. The tubular extension 124 on the suction fitting 122 is connected to a vacuum source to produce suction through the lumen of the shaft 120, and the suction is bypassed from the jaws 24 and 26 due to the push ring 142 being biased by the suction spring 148 to uncover the suction diverting holes 140 communicating with the window 100 and the port 104 in the handle body 28 as shown in FIG. 8.

Accordingly, the suction forceps can be introduced easily into the surgical site with no suction at the jaws. When it is desired to cut tissue at the surgical site, the operating handles 98 and 150 are manually grasped and squeezed by the surgeon causing the movable handle 150 to pivot, or rotate, around the pivot pin 158. As the hand grip 152 on the movable handle 150 is rotated toward the fixed handle 98, the fingers 162 on the actuating end 154 move in the distal direction against the rearward shoulder 146 of the push ring 142 to overcome the biasing force of the suction spring 148 and slide the push ring 142 in the distal direction relative to the shaft 120. Rotation of the movable handle 150 approximately one-half the full rotational extent of the handle 150 causes the suction spring 148 to be compressed between the clip 128 and the forward shoulder 144 of the push ring 142 and the push ring 142 to be moved into a position covering the suction diverting holes 140 to produce suction in the suction passage defined by the lumens of the shaft 120, the inner member 18 and the cam 66 to establish suction in the chamber 40 via the aperture 72 in the cam 66. While in an open position, the jaws 24 and 26 are positioned to engage tissue, and the suction draws the tissue between the jaws 24 and 26. The aperture 72 being proximally spaced from the jaws 24 and 26 produces a distribution of suction around the jaws 24 and 26 such that tissue is drawn through the opening 38 into the chamber 40 to be optimally positioned for precision cutting. Further rotation of the movable handle 150 causes the fingers 162 acting against the push ring 142 to overcome the biasing force of the actuating spring 132 against the clip 128 and slide the shaft 120 in the distal direction within the upper passage 92. The shaft 120 slides the inner member 18 and, therefore, the cam 66, in the distal direction relative to the outer member 12 causing the actuator 76 to pivot, or rotate, the movable jaw 26 downwardly in a forward, or distal, direction through the opening 38 to position the distal end wall 50 adjacent the distal end of the opening 58 and move the cutting edges 54 and 56 on the movable jaw 26 past the cutting edge on the inner surface of the stationary jaw 24 to a closed position to cut tissue through the opening 58. The cut tissue is aspirated from the chamber 40 through the suction passage to exit the suction forceps via the suction fitting 122, the suction passage having no constrictions therein to obstruct tissue flow. When the jaws 24 and 26 are in the closed position, suction is still produced at the surgical site continuously via the aperture 44 in the stationary jaw 24 to facilitate movement of cut tissue through the instrument. When the handles 98 and 150 are released, the actuating spring 132 moves the shaft 120 in the proximal direction such that the stop 134 on the shaft 120 abuts the washer 138 adjacent the suction fitting 122, the movement of the tubular shaft 120 causing the actuator 76 to pivot the movable jaw 26 to the open position as shown in FIG. 4. The suction spring 148 moves the push ring 142 in the proximal direction to uncover the suction diverting holes 140 and urge the fingers 162 of the movable handle 150 against the stop 134.

For safety in handling and to facilitate manipulation during insertion and positioning at a surgical site, the jaws 24 and 26 can be locked in the closed position by manually holding the handle 150 in a rotated position corresponding to the closed position for the jaws 24 and 26 while manually moving the locking pin 178 via the end caps 182 from the unlocked position at the lowermost ends of the slots 180 to the locked position at the uppermost ends of the slots 180, wherein the locking pin 178 is retained by the beads 190 on the spring latches 188 to be secured against accidental displacement from the locked position. When the handle 150 is then released, the locking pin 178 engages tip 186 on the plunger 184 and prevents the movable handle 150 from automatically returning to a position corresponding to the open position for the jaws 24 and 26 as shown in FIG. 3. The jaws 24 and 26 are thereafter opened by manually grasping the end caps 182 and moving the locking pin 178 to the lowermost ends of the slots 180, such movement being permitted by temporary deflection of the spring latches 188 outwardly from the slots 180 to permit the movable handle 150 to automatically return to a position corresponding to the open position for the jaws 24 and 26 under the bias force of the actuating spring 132. The tip 186 on the plunger 184 is then disposed in the path of movement of the locking pin 178 and prevents movement of the locking pin 178 to the locked position when the movable handle 150 is not in a rotated position corresponding to the closed position for the jaws 24 and 26.

When an operating force is applied to the movable handle 150 exceeding a predetermined force determined by the force diverting mechanism cooperating with springs 172 and 177, such as when attempting to cut very large quantities of or very hard tissue between the jaws 24 and 26, at least a portion of the force is diverted against the biasing force of the springs to move the pivot pin 158 and provide a tactile indication to the surgeon of the excessive force being applied such that the applied force can be reduced without damage to or breakage of components at the distal end of the forceps. The elbow 153 of the movable handle 150 moves away from the forward wall of the vertical passage 96 in opposition to the overload spring 172, and the pivot pin 158 moves with the handle 150. The handle 150, thus, pivots around a second pivot point, and the projecting ends of the pivot shaft 158 move visibly from the forwardmost ends of the tracks 160 toward the rearwardmost ends of the tracks. By placing a finger against the tracks 160, a surgeon can also feel the ends of the pivot pin 158 moving within the tracks. The tension or resistance felt on the handle 150 and the movement of the pivot pin 158 tactilely and visually indicate when a potentially damaging operating force is applied through the handle 150 and permit the operator to "ease off" on the handle 150 and take a smaller "bite" of tissue prior to the suction forceps being damaged or disabled. Once the operating force applied to the movable handle 150 falls below the predetermined force, the overload spring 172 automatically positions the elbow 153 to engage the forward wall of the vertical passage 96 and the pivot shaft 158 at the forwardmost ends of the tracks 160. The compressor 174 can be positioned a selected longitudinal distance in the lower passage 94 to obtain a desired state of compression for the overload spring 172 to thereby selectively adjust the magnitude of the operating force that can be applied via the handle 150 before the predetermined force is reached. Additionally, it will be appreciated that excessive force applied to the handles is taken up or diverted by movement of the pivot pin 158 against the spring bias rather than being transmitted to the jaws. In this manner, the jaws are protected eliminating the possibility of breakage at the distal end of the suction forceps in the surgical site.

The suction grasping forceps of FIG. 7 is operated in the same manner as previously described with the jaws 224 and 226 being utilized to grasp tissue. Suction produced in the chamber 240 in the stationary jaw 224 initially draws tissue between the jaws 224 and 226 when the jaws are in the open position such that tissue proximate but in less than direct engagement with the jaws 224 and 226 can be drawn into the chamber 240. The suction assists in positioning and holding the tissue between the jaws 224 and 226 when the jaws are closed around the tissue to facilitate use of the jaws and permit the tissue to be pulled upon and manipulated with the jaws.

The suction cutting forceps of FIG. 9 is operated in the same manner as previously described; however, with the shaft 120 biased against the suction fitting 122 by the actuating spring 132, the actuator 76 is positioned centrally in the chamber 340 between the distal wall 341 and the proximal wall 343. The pivot pins 329 and 364 are substantially longitudinally aligned, and the cutting portion of the movable jaw 326 extends downwardly through the opening 338 and proximally from the pivot point 327 such that the cutting edges 354 and 356 face in a proximal, or rearward, direction as shown in FIG. 9. When the tubular shaft 120 and, therefore, the inner member 18, are slid in the distal direction, the actuator 376 is moved forwardly by the cam 366, and the movable cutting jaw 326 is pivoted by the actuator to position the flats 345 on the actuating portion of the movable jaw 326 in to engagement with the distal wall 341 of the chamber 340 and the end wall 350 of the movable jaw 326 in engagement with the proximal cutting edge 339 as the cutting edges 354 and 356 move upwardly through the opening 338 into the chamber 340. Therefore, the movable jaw 326 can be positioned over and forwardly of tissue to be cut and then pivoted or rotated in a proximal, or rearward, direction to grab and scoop up the tissue into the opening 338 for cutting when the cutting edges 354 and 356 on the movable jaw 326 move past the opening 338 in a rearwardly directed "backbiting" cutting action. Suction is provided at the surgical site continuously with suction produced at the jaws via the aperture 344 in the stationary jaw 324.

Having described preferred and alternative embodiments of a new and improved suction forceps, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical forceps for engaging tissue in the body comprising:
   an elongate probe including an outer tubular member having a proximal end and a distal end and an inner member movable within said outer probe member and having a proximal end and a distal end;
   jaw means for engaging tissue including a first jaw coupled with said outer probe member distal end and a second jaw coupled with said inner probe member distal end and mounted for pivotal movement relative to said first jaw in response to movement of said inner probe member within said outer probe member;
   handle means coupled with said outer probe member proximal end and said inner probe member proximal end for moving said inner probe member relative to said outer probe member and pivoting said second jaw relative to said first jaw, said handle means including hand grip members squeezable to impart a force to pivot said first jaw via movement of said inner probe member; and
   force diverting means coupled with said handle means for diverting at least a portion of a force applied to said grip members from said jaw means when the applied force exceeds a predetermined force, said force diverting means including movable pivot means for pivotally mounting one of said grip members, said pivot means being automatically moved closer to the other of said grip members when the applied force exceeds said predetermined force.

2. A surgical forceps as recited in claim 1 wherein said force diverting means is coupled with said grip members for providing a tactile indication of the applied force exceeding said predetermined force via said grip members.

3. A surgical forceps as recited in claim 1 wherein said handle means includes means for movably supporting said pivot means.

4. A surgical forceps as recited in claim 3 wherein said handle means includes a body mounting said grip member, said supporting means includes slots in said body, and said pivot means includes a pivot pin having opposing ends movably received in said slots.

5. A surgical forceps as recited in claim 4 wherein said body includes spaced parallel walls and said slots are formed in said walls.

6. A surgical forceps as recited in claim 5 wherein said force diverting means includes means for biasing said pivot pin against movement in said slots when the applied force is less than said predetermined force and permitting movement of said pivot pin in said slots when the applied force exceeds said predetermined force.

7. A surgical forceps as recited in claim 6 wherein said body includes an upper passage between said side walls and a lower passage between said side walls in parallel with said upper passage, said handle means includes actuating means connecting said one grip member with said inner probe member proximal end and disposed in said upper passage, said bias means is disposed in said lower passage, said pivot pin is disposed in said body in longitudinal alignment with said lower passage, and said force diverting means includes means for holding said pivot pin in engagement with said bias means including a disk disposed in said lower passage in engagement with said bias means and a projection on said disk having a notch therein for retaining said pivot pin.

8. A surgical forceps as recited in claim 7 wherein said bias means includes a helical spring mounted in compression in said lower passage and means for selectively compressing said spring against said holding means.

9. A surgical forceps as recited in claim 1 wherein said first and second jaws have peripheral cutting edges for severing tissue, said inner probe member is tubular, and said handle means has a passage therethrough terminating at a suction fitting, said inner probe member and said handle means passage forming a suction passage for aspirating cut tissue through said surgical forceps.

10. A surgical forceps as recited in claim 1 wherein said first and second jaws carry cooperatively interengagable grasping teeth for holding tissue therebetween, said inner probe member is tubular, and said handle means has a passage therethrough terminating at a suction fitting, said inner probe member and said handle means passage forming a suction passage for assisting grasping of tissue between said first and second jaws.

11. A surgical forceps for engaging tissue in the body comprising
an elongate probe including an outer tubular member having a proximal end and a distal end and an inner member movable within said outer probe member and having a proximal end and a distal end;
jaw means for engaging tissue including a first jaw coupled with said outer probe member distal end and a second jaw coupled with said inner probe member distal end and mounted for pivotal movement relative to said first jaw in response to movement of said inner probe member within said outer probe member;
handle means coupled with said outer probe member proximal end and said inner probe member proximal end to moving said inner probe member relative to said outer probe member and pivoting said second jaw relative to said first jaw, said handle means including hand grip members squeezable to impart a force to pivot said first jaw via movement of said inner probe member; and
force diverting means coupled with said handle means for diverting at least a portion of a force applied to said grip members from said jaw means when the applied force exceeds a predetermined force, said force diverting means including movable pivot means for pivotally mounting one of said grip members, said pivot means including a pivot pin and being movable when the applied force exceeds said predetermined force, said force diverting means including means for biasing said pivot pin away from the other of said grip members with a force corresponding to said predetermined force and permitting said pivot pin to move against said bias means when the applied force exceeds said predetermined force, said force diverting means being coupled with said grip members for providing a tactile indication, via said grip members, of the applied force exceeding said predetermined force.

12. A surgical forceps as recited in claim 11 wherein said handle means includes means for permitting visualization of movement of said pivot pin.

13. A surgical forceps for engaging tissue in the body comprising
an elongate probe having a distal end and a proximal end;
jaw means mounted on said probe distal end for movement between an open position and a closed position to engage tissue;
handle means coupled with said probe proximal end and including a handle body and first and second hand grip members extending from said handle body, one of said hand grip members being movable relative to said handle body and the other of said hand grip members for moving said jaw means between said open and closed positions; and
locking means carried by said handle body for selectively locking said jaw means in said closed position, said handle body including track means for guiding movement of said locking means to said locked position and said locking means including a pin having opposing ends received in said track means, said locking means being selectively movable in said handle body to a locked position engaging said handle body and only one of said grip members, said locking means being movable to said locked position only when said jaw means is in said closed position, said handle means including means for preventing movement of said locking means to said locked position when said jaw means is not in said closed position and latch means for securing said locking means in said locked position.

* * * * *

UNITED STATES PATENT AND TRADEMARK OFFICE
CERTIFICATE OF CORRECTION

PATENT NO. : 5,286,255
DATED : February 15, 1994
INVENTOR(S) : Robert M. Weber

It is certified that error appears in the above-indentified patent and that said Letters Patent is hereby corrected as shown below:

On the title page, in the Abstract, line 8, after "or" (second occurrence) insert --to--.

Column 1, line 66, delete "o" and insert --or--.

Column 7, line 8, delete "When" and insert --when--.

Column 8, line 50, after "the" (second occurrence) insert --actuator--.

Column 11, line 28, after "in" delete "to".

Column 12, line 24, delete "member" and insert --members--.

Signed and Sealed this

Twenty-first Day of June, 1994

Attest:

BRUCE LEHMAN

*Attesting Officer*     *Commissioner of Patents and Trademarks*